US008591966B2

(12) United States Patent
Kreuter

(10) Patent No.: US 8,591,966 B2
(45) Date of Patent: Nov. 26, 2013

(54) COMPOSITION CONTAINING OILS OF CHAMOMILE FLOWER AND BLACK CUMIN WITH REDUCED ENDOTOXINS

(75) Inventor: Matthias Heinrich Kreuter, Walenstadt (CH)

(73) Assignees: Insignion Holdings Limited, Hamilton (BM); Veritron Limited, London (GB)

( * ) Notice: Subject to any disclaimer, the term of this patent is extended or adjusted under 35 U.S.C. 154(b) by 614 days.

(21) Appl. No.: 12/602,272

(22) PCT Filed: Jun. 2, 2008

(86) PCT No.: PCT/GB2008/001849
§ 371 (c)(1),
(2), (4) Date: Nov. 30, 2009

(87) PCT Pub. No.: WO2008/146009
PCT Pub. Date: Dec. 4, 2008

(65) Prior Publication Data
US 2010/0178368 A1    Jul. 15, 2010

(30) Foreign Application Priority Data

Jun. 1, 2007   (GB) .................................. 0710536.4

(51) Int. Cl.
*A61K 36/28*   (2006.01)
*A61K 36/23*   (2006.01)
(52) U.S. Cl.
USPC ........................................... 424/764; 424/725
(58) Field of Classification Search
USPC ................................................. 424/725, 764
See application file for complete search history.

(56) References Cited

U.S. PATENT DOCUMENTS

| 6,300,370 B1 * | 10/2001 | Carle et al. ..................... 514/464 |
| 2005/0208179 A1 * | 9/2005 | Albrecht et al. ................ 426/72 |
| 2009/0169659 A1 * | 7/2009 | Kreuter ......................... 424/764 |

FOREIGN PATENT DOCUMENTS

| DE | 202006019183 | * | 5/2007 |
| JP | 2005-519055 | | 6/2005 |
| JP | 2006-510592 | | 3/2006 |
| WO | WO 03/033007 A1 | | 4/2003 |
| WO | WO 03/101479 A1 | | 12/2003 |
| WO | WO 2005/070440 A1 | | 8/2005 |
| WO | WO 2007/057651 | * | 5/2007 |
| WO | WO 2007/057651 A1 | | 5/2007 |

OTHER PUBLICATIONS

Leutjohann The Healing Power of Black Cumin; 1997, Lotus Light Publications; Twin Lakes, WI, pp. 140-141.*
Higley et al. Reference Guide for Essential Oils; 2005; Abundant Health Publisher, Spanish Fork, UT; p. 330.*
Lawless The Illustrated Encyclopedia of Essential Oils; 1995, Harper Collins Publishers, Hammersmith, London, p. 168.*
International Search report of Appln No. PCT/GB2008/001849 dated Aug. 19, 2008.
International Preliminary Report on Patentability dated Jun. 25, 2009.

(Continued)

*Primary Examiner* — Patricia Leith
(74) *Attorney, Agent, or Firm* — Buchanan Ingersoll & Rooney PC

(57) ABSTRACT

A composition comprising an aqueous extract of camomile flowers is useful for the treatment of a proliferative and/or inflammatory condition.

20 Claims, 8 Drawing Sheets

(56) References Cited

OTHER PUBLICATIONS

Uteshev et al., Eksp. Klin. Farmakol. "Immunomodulating Activity of Heteropolysaccharides of *Matricaria chamomilla* L. Upon Air and Immersion Cooling" (Nov.-Dec. 1999) 62(6):52-55, Russian State Medical University, Ostrovityanova str., 1, 117869, Moscow, Russia (with English language abstract).

Laskova and Uteshev, "Immunomodulating Action of Heteropolysaccharides Isolated From Camomile Flower Clusters", Antibiot. Khimioter. (Jun. 1992) 37(6):15-18, N. I. Pirogov 2nd Moscow Medical Institute (with English language abstract).

Fueller E. et al., "Anti-Inflammatory—Activity of Chamomile Polysaccharides" *Pharmaceutical and Pharmacological Letters*, (2000) 2:86-87 Medpharm, Scientific Publ., Stuttgart, DE.

Barene Ilze et al., "The Complex Technology on Products of German Chamomile", *Medicina, Kauno Medicinos Universitetas* (Kaunsas University of Medicine), LT, vol. 39, No. suppl 2, (Jan. 1, 2003), pp. 127-131.

Srivastava Jammejai K. et al., "Anti-Proliferative and Apoptotic Effects of Chamomile Extract in Various Human Cancer Cells", *Proceedings of the American Association for Cancer Research Annual Meeting*, vol. 48, (Apr. 2007) pp. 997.

Hajhasemi Valiollah et al., Black Cumin Seed Essential Oil, as a Potent Analgesic and Antiinflammatory Drug, Phytotherapy Research: PTR (Mar. 2004), vol. 18, No. 3, 195-199, Mar. 2004.

El Gazzar et al., "Downregulation of Leukotriene Biosynthesis by Thymoquinone Attentuates Airway Inflammation in a Mouse model of Allergic Asthma" *Biochimica et Biophysica Acta—General Subjects*, Elsevier Science Publishers, NL, vol. 1760, No. 7, (Jul. 1, 2006), pp. 1088-1095.

Japanese Office Action mailed on Jun. 11, 2013, issued in corresponding JP Patent Application No. 2010-509896.

Sashidhara, KV, et al., Essential oil composition of *Matricatia recutita* L. from the lower region of the Himalayas, Flavour Frag J 21(2): 274-276 (2006).

Houghton PJ, et al., Fixed oil of *Nigella sativa* and derived thymoquinone inhibit eicosanoid generation in leukocytes and membrane lipid peroxidation, Planta Med 61(1): 33-6 (1995).

* cited by examiner

US 8,591,966 B2

COMPOSITION CONTAINING OILS OF CHAMOMILE FLOWER AND BLACK CUMIN WITH REDUCED ENDOTOXINS

FIELD OF THE INVENTION

This invention relates to a plant extract and its therapeutic use, i.e. a composition comprising an aqueous extract of camomile flowers for the treatment of a proliferative and/or inflammatory condition, the use of said composition for the manufacture of a medicament for the treatment of a proliferative and/or an inflammatory condition, and a method for the treatment of a proliferative and/or inflammatory condition, which comprises administering to a human or animal patient in need thereof, in an effective amount, said composition.

The invention relates particularly to a composition comprising an aqueous extract of chamomile flowers for the treatment of a proliferative and/or inflammatory condition, wherein the chamomile flowers are *Flores tubiformis*. The invention relates further to the use of said composition, characterised in that the condition is cancer, preferably a glioblastoma or lung cancer or prostate cancer. The invention relates also to the use of said composition for the manufacture of a medicament for the treatment of an inflammatory condition, more preferably Morbus Chron, most preferably multiple sclerosis.

BACKGROUND OF THE INVENTION

The therapeutic properties of various plants have been known for millennia. Even today, however, the nature of the effective component or components and their properties are little understood, even for those plants that have been studied, since pharmaceutical development generally focuses on small molecules that are deemed to have relatively predictable properties and whose synthesis can be controlled.

Uteshev et al, Eksp. Klin. Farmakol. (1999 November-December) 62(6):52-5, describes the immunomodulating activity of heteropolysaccharides obtained from German chamomile (*Matricaria chamomilla*) during air and immersion cooling. Laskova and Uteshev, Antibiot. Khimioter. (1992 June) 37(6):15-8, describes the immunomodulating action of heteropolysaccharides isolated from camomile flowers. The water-based extract was administered orally or by intraperitoneal injection. The authors do not suggest any therapeutic utility, but rather report that the stimulatory effect is dependent on dosing regime and, primarily, the manner and degree of cooling of the tested rats.

WO2005/070440 relates to the use of a herbal formula for treatment of allergic asthma or chronic bronchial asthma, comprises specific amounts of dried and grinded camomile flowers, anis fruits, black seeds etc. administered as tea infusion.

WO03/101479 describes the valuable therapeutic properties of a composition comprising several components, typically given together by intramuscular injection. The composition that was used comprises a camomile extract, although no therapeutic activity is ascribed to it; rather, it is described as an anti-irritant whose presence may alleviate the unpleasant effect of the injection per se.

WO2007/057651 discloses a process for the removal of endotoxins from camomile.

SUMMARY OF THE INVENTION

Surprisingly, it has now been found that a camomile extract, obtained from the flower heads, preferably obtained by steam distillation, has valuable therapeutic properties. Such aqueous extracts are known to consist of the volatile components of the camomile flower heads and are described in the European Pharmacopeia (Matricariae aetheroleum PhEur 5, corrected.5.1).

In particular, it has been found that said extracts can reduce DNA synthesis in human cancer cells and inhibit the production of leucotrienes and IL-6 (interleukin 6). More surprisingly, it has been found that the inhibition of leucotriene synthesis of the volatile oil is potentiated synergistically in the presence of the seed oil of black cumin (*Nigella sativa*).

Especially cancer cells, which are known to produce interleukin 6 as a growth factor by their own and cancer cells, which are known to produce leucotrienes by their own, were found to be sensitive. It may be deduced that the volatile oil of camomile alone and a combination with black cumin seed oil has up to day unexpected anti-inflammatory and anticancer properties, e.g. in the treatment of inflammation, immunopathy and cancer.

Accordingly, the invention relates to
(1) a composition comprising an aqueous extract of camomile flowers for the treatment of a proliferative and/or inflammatory condition;
(2) the composition according (1), wherein the aqueous extract is a volatile oil, which is obtainable by an extraction process comprising a water steam distillation of camomile flowers, preferably under reduced pressure;
(3) the composition according to (1) or (2), wherein the camomile flowers are *Flores tubiformis;*
(4) the composition according to (2) or (3), wherein the steam distillation is performed under nitrogen atmosphere and the process further comprises the steps of
   (i) contacting the composition with a crosslinked povidone that forms a complex with coumarins;
   (ii) removing the complex of crosslinked povidone and coumarin formed in step (i);
   (iii) removing water residues by contacting the composition obtained from step (ii) with anhydrous sodium sulfate; and
   (iv) separating the sodium sulfate from the composition obtained in step (iii);
(5) the composition according to any of (1) to (4), wherein the composition additionally comprises black cumin oil;
(6) the composition according to (5), wherein black cumin oil is a purified black cumin oil obtainable by a purification process comprising the steps of
   (i) contacting black cumin oil with a cross-linked povidone that forms a complex with phenolic compounds;
   (ii) removing the complex of crosspovidone and phenolic compounds formed in step (i);
   (iii) removing water residues by contacting the black cumin oil obtained from step (ii) with anhydrous sodium sulfate; and
   (iv) separating the sodium sulfate from the black cumin oil obtained in step (iii);
(7) the composition according to any of (1) to (6), characterised in that the condition is an inflammatory condition, preferably selected from the group consisting of Morbus Chron and multiple sclerosis;
(8) the composition according to any of (1) to (6) characterised in that the condition is cancer, preferably selected from the group consisting of glioblastoma, lung cancer and prostate cancer;
(9) the composition according to any of (1) to (7), characterised in that the inflammatory condition is caused by autoimmunopathy, preferably triggered by interleukin 6, more preferably triggered by leucotrienes, most preferably dependent on the presence of interleukin 6 and/or leucotrienes;

(10) the composition according to any of (1) to (6) and (8), characterised in that the condition is caused by a proliferative disorder, preferably triggered by interleukin 6, more preferably triggered by leucotrienes, most preferably dependent on the presence of interleukin 6 and/or leucotrienes;

(11) use of the composition as defined in any of (1) to (6) for the manufacture of a medicament for the treatment of a proliferative and/or an inflammatory condition;

(12) the use according to (11), wherein the condition is as defined in any of (7) to (10);

(13) a method for the treatment of a proliferative and/or inflammatory condition, which comprises administering to a human or animal patient in need thereof, in an effective amount, a composition as defined in any of (1) to (6); and

(14) the method according to (13), wherein the condition is as defined in any of (7) to (10).

DESCRIPTION OF THE INVENTION

The invention is based on data obtained using an aqueous extract of camomile flower heads, preferably obtainable by steam distillation. Precisely the aqueous extract is composed of the volatile components of the flower heads of *Matricaria recutita* L., also known for those skilled in the art as Matricariae aetheroleum, described in PhEur 5.1. The invention is based further on data obtained by using a combination of black cumin seed oil and the volatile oil of the camomile flower heads.

The extract may be obtained by any suitable procedure, including methods known to those of ordinary skill in the art. The extract may be obtained by using an aqueous or organic medium, and separated from other components by filtration, chromatography, supercritical fluid extraction etc. For example, a material that may be used in the invention is derived from the dried flower heads of the Asteraceae plant *Matricaria recutita* L. or one or more materials therein, including volatile oils, chamazulene, bisabolol and other substances. A preferred procedure is to purify the initially obtained volatile oil by contacting it with crosspovidone (crosslinked povidone) and sodium sulfate. Crosspovidone is known for those skilled in the art to complex phenolic compounds and coumarins. The volatile oil of camomile flowers may be filtered using a filter having a pore size of from 0.001 to 0.02 μm. Sodium sulfate is known to bind residues of water. Separation of the purifying agents results in an coumarin, phenol and water residue free or nearly free extract. The source of the camomile extract is important. It should be the flower head, preferably the tubular flowers of *Matricaria recutita* L. (*Flores tubiformis*). The composition may contain beside the volatile oil of camomile the seed oil of black cumin and acetylcysteine and ascorbyl palmitate as active ingredients. No other agent need be present.

The composition may contain less than 0.01% w/w coumarins measured as 7-hydroxycoumarin. The composition may also contain less than 0.01% w/w of water. The composition also may be free or essentially free of compounds selected from coumarins, flavonoids and residual water. The composition may also contain chamazuline in an amount of 5-15% w/w The composition that is used should be suitable for injection. For this purpose, it is desirable to remove endotoxins, polyphenols, cumarines and (by any suitable means, known to those in the art) large molecular weight component, e.g. those having a m. wt. of more than 1,000 or 10,000.

The composition, after endotoxin removal, may contain endotoxins in an amount of 100 EU/ml. EU/ml is endotoxin units per ml which is a European Pharmacopoeia (Ph. Eur.) unit. and also may contain no material having a molecular weight in excess of 10,000.

Compositions for use in the invention can be formulated by methods known to those skilled in the art. Pharmaceutically acceptable components should be used. The term "pharmaceutically acceptable" refers to those properties and/or substances which are acceptable to the patient from a pharmacological/toxicological point of view and to the manufacturing pharmaceutical chemist from a physical/chemical point of view regarding factors such as formulation, stability, patient acceptance and bioavailability.

Administration is preferably by intravenous or, more preferably, intramuscular injection, yet most preferably by an inhalator as an aerosol or micro/nano-emulsion via the respiratory tract.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients such as, for example, inert diluents such as calcium carbonate, sodium carbonate, lactose, calcium phosphate or sodium phosphate; granulating and disintegrating agents, for example corn starch or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated, to form osmotic therapeutic tablets for control release.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions may contain the active materials in admixture with suitable excipients. Such excipients are suspending agents, for example sodium carboxymethylcellulose, methylcellulose, hydroxypropylmethyl-cellulose, sodium alginate, polyvinyl pyrrolidone, gum tragacanth and gum acacia; dispersing or wetting agents, for example a naturally occurring phosphatide such as lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, such as a polyoxyethylene with partial esters derived from fatty acids and hexitol anhydrides, for example polyoxyethylene sorbitan monooleate. Aqueous suspensions may also contain one or more preservatives, for example ethyl or n-propyl p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents (such as those set forth above) and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified above. Sweetening, flavouring and colouring agents may also be present.

A pharmaceutical composition for use in the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated using suitable dispersing or wetting agents and suspending agents, examples of which have been mentioned above. A sterile injectable preparation may also be in a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The composition may also be administered in the form of suppositories for rectal administration of the drug. Such compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, suitable compositions are in the form of, for example, creams, ointments, jellies, solutions or suspensions.

As indicated above, composition of the invention may be given by injection. Intramuscular injection is preferred, although any parenteral administration is suitable.

It may also be preferred that the composition is given orally. In this case, and in the event that the permeability-increasing agent is used, insulin should not be included in an oral formulation. Oral administration may be particularly preferred for veterinary medicine.

Other active materials may also be given to the subject. Although it is not believed that further materials are necessary, it has been found that certain steroids and vitamins, typically given orally, can support or enhance the effect of the medicament. Suitable steroid hormones may increase the synthesis of specific proteins, by unmasking certain cistrons, with the assistance of essential metabolites such as vitamins and amino acids. Examples of suitable steroids are estradiol, nandrolone and estriol. Vitamins such as A, D and/or E may also be given. The function of vitamin A may be to preserve the integrity of epithelial tissue, to play a role in protein synthesis, and to stabilise cell membranes and also subcellular membranes.

Although some indication has been given as to suitable dosages of certain materials, the exact dosage and frequency of administration depend on several factors. These factors include the particular components that are used, the particular condition being treated, the severity of the condition, the age, weight and general physical condition of the particular patient, and other medication the individual may be taking, as is well known to those skilled in the art.

EXAMPLES

Figure 1A:
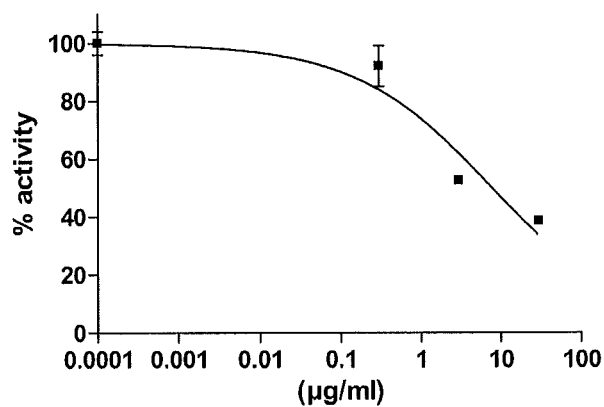
FIG. 1A shows the results of the IL-6 inhibition replication 1 in Example 1 for *Matricaria* essential oil:
VIP_Matr'07_78
IC50=5 µg/ml (graphically determined)
PRISM IC50=7.782 µg/ml (calculated by GraphPad Prism)
95% interval 3.169 to 19.11
Figure 1B:
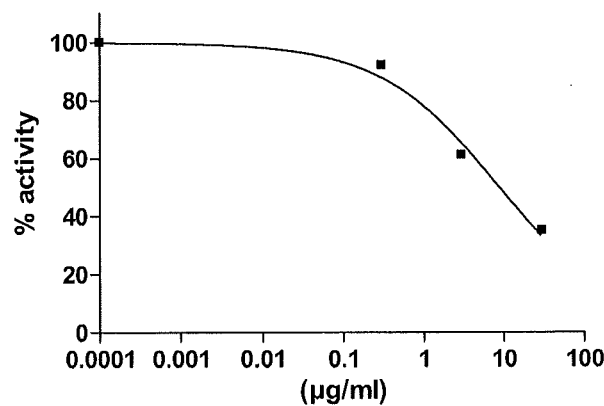
FIG. 1B shows the results of the IL-6 inhibition replication 2 in Example 1 for *Matricaria* essential oil:
VIP_Matr'07_78
IC50=8 µg/ml (graphically determined)
PRISM IC50=8.78 µg/ml (calculated by GraphPad Prism)
95% interval 6.248 to 12.35 µg/ml
Figure 1C:
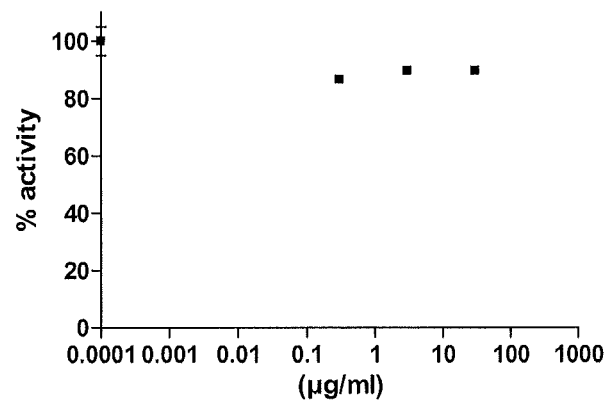
FIG. 1C shows the results of the IL-6 inhibition replication 1 in Example 1 for *Nigella* essential oil:
VIP_Nig'07_8
IC50=not applicable
PRISM IC50=does not converge (GraphPad Prism)
95% interval
Figure 1D:
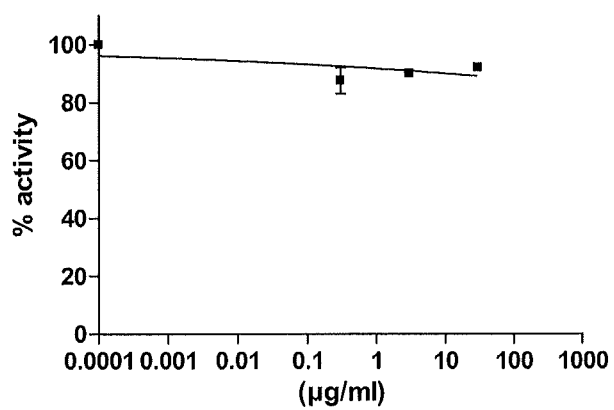
FIG. 1D shows the results of the IL-6 inhibition replication 2 in Example 1 for *Nigella* essential oil:
VIP_Nig'07_8
IC50=not applicable
PRISM IC50=does not converge (GraphPad Prism)
95% interval

The following Examples further illustrate the invention.

Example 1

Inhibitory Activity in THP1 (Macrophages) on Interleukin 6 Release

| Samples and reference substances | | | | | |
|---|---|---|---|---|---|
| Test samples | Description | Provider | Art. No | Batch No. | ViP Number |
| *Nigella* oil | Nigellae oleum | Hänseler AG | 26-4150-1 | 2006.08.0537 | ViP__Nig'07__8 |
| *Matricaria* essential oil | Matricariae Aetheroleum PhEur | Hänseler AG | 1-4925-2 | 2006.09.0181 | ViP__Matr'07__78 |

| Reference substances | Order No. | Batch No. | Supplier | Assay |
|---|---|---|---|---|
| NDGA | 74540 | 422 780/1 5400 | Fluka | 5-LOX inhibition on diff. HL-60 cells |

| IL-6 inhibition assay | | | | | |
|---|---|---|---|---|---|
| Assay | Cell line | Sample | Sample concentration in assay (based on weight of oil) | Solvent | Replication |
| IL-6 Inhibition* | THP 1 differentiated | ViP__Nig'07__8 | 300 ng, 3 µg, 30 µg/ml | EtOH abs. | 2 |
| | | ViP__Matr'07__78 | 300 ng, 3 µg, 30 µg/ml | s.o. | 2 |

*The assay was performed in two independent replications

\* The assay was performed in two independent replications
IL-6 Inhibition Assay on THP-1 Cells The samples were preincubated for 30 minutes at 37° C. with cells (human THP-1) previously differentiated with PMA ($0.125 \times 10^6$ cells/well). The reaction was started with LPS (1 ug/ml) and the incubation was performed over 24 hours at 37° C. Negative controls t(0) were carried out with the assay mixture without LPS-stimulation [ref.1].

The quantification of IL-6 was performed with an Enzyme Immuno Assay (EIA) Kit from Cayman No: 583361. The optical densities were measured at wavelength=415 nm. The quantities were calculated using a standard curve of at least 5 different concentrations.

Each sample points were measured as duplicates. The dose related inhibition values were expressed as a percentage of the positive control values. The IC50 values (corresponding to the sample concentration at which the inhibition level is 50%) were determined with the program GraphPad-Prism (Version 4, GraphPad Software Inc., San Diego, Calif., USA).

Results

The results for Example 1 are shown in FIG. 1.

Example 2

Inhibitory Activity of NICHA 001 in Human Cancer Cell Lines on Leucotriene Release The response of two human cell lines (granulocytes) under different concentrations of NICHA on leucotriene release were investigated. Each experiment was done with *Nigella* oil, with chamomile oil and with a combination of both oils.

| Samples | | | | | |
|---|---|---|---|---|---|
| Test samples | Description | Provider | Art. No | Batch No. | ViP Number |
| *Nigella* oil | Nigellae oleum | Hänseler AG | 26-4150-1 | 2006.08.0537 | ViP__Nig'07__8 |
| *Matricaria* essential oil | Matricariae Aetheroleum PhEur | Hänseler AG | 1-4925-2 | 2006.09.0181 | ViP__Matr'07__78 |

Assays

| Assays | Cell lines | Samples | Test concentrations |
|---|---|---|---|
| 5-LOX inhibition | Granulocytes differentiated HL60 | ViP_Nig'07_8 | 0.3/3/30 µg/ml |
| | | ViP_Matr'07_78 | 0.1/0.3/1/3/10/30 µg/ml |
| | | Mixture | 0.3/3/30 µg/ml |
| WST-1 assay | HL-60 cells | ViP_Nig'07_8 | 0.3/3/30 µg/ml |
| | | ViP_Matr'07_78 | |

5-LOX Inhibition Assay

Human HL-60 cells (myeloid leukemia, DSMZ No ACC 3) were kept at 37° C. in a humidified atmosphere with 5% $CO_2$ and cultured in complete RPMI1640 medium supplemented with 10% fetal calf serum and 1% (v/v) penicillin/streptomycin solution. Cells were differentiated for 6 to 8 days with DMSO (1.2% v/v). The 5-LOX activity assay was carried out as described by Bennet et al. [ref: 2]. Briefly, differentiated cells were harvested, suspended in PBS containing $Ca^{2+}$ (1 mM) and glucose (1 mM) and distributed into a 96-well microtiter plate ($1\times10^6$ cells/well).

After preincubation with sample or vehicle for 15 min at room temperature the reaction was started by adding calcium ionophore A 23187 (5 uM) and arachidonic acid (10 uM). All values are final concentrations. Negative controls were carried out without calcium ionophore stimulation. The assay mix was incubated for 15 min at 37° C. and terminated by adding 100 µl methanol containing HCl (1 M, 3% v/v) and placing the microtiter plate on ice. After neutralization with 50 µl PBS and centrifugation (340×g) for 10 min the $LTB_4$ concentration in the supernatant was determined.

Effects of samples and reference compound [ref: 3] on the activity of 5-LOX were measured by determining the quantity of leukotriene $B_4$ produced under assay conditions. The quantification of leukotriene $B_4$ was performed with Enzyme Immuno Assay (EIA) Kit from Cayman No 520111 ($LTB_4$).

The optical densities were measured at wavelength=415 nm. The quantities were calculated using a standard curve of at least 5 different concentrations. Sample points were measured as duplicates. The dose related inhibition values were expressed as a percentage of the positive control values. If applicable the $IC_{50}$ values (corresponding to the sample concentration at which the inhibition level is 50%) were determined with the program GraphPad-Prism (Version 4, GraphPad Software Inc., San Diego, Calif., USA).

Viability Assay on HL60 with WST-1

Cell function/mitochondria: the decrease of metabolic activity [ref: 4] was tested on human hepatocytes (Hep G2), human granulocytes (differentiated HL60), human monocytes (THP-1) and human macrophages (differentiated THP-1) with a Tetrazoliumsalt WST-1 Kit (Biovision, K301-500, CA USA). The cells were pre-incubated with extract for 24 hours.

The metabolic activity of the cells was measured by the ability of living cells to reduce the tetrazolium salt WST-1 to formazan. The quantity of formazan was measured directly by determining the optical density (OD) with a plate reader (BioRad, USA) at a wavelength of $\lambda=450$ nm.

The optical measurements were performed as triplicates and standard deviations were calculated. For each test concentration the OD values of the blank (assay mixture with samples but without cells) was subtracted from the average of the OD measurements with cells. OD450-values were transformed into percentage values with viability readings of 100% corresponding to measurements of the control without sample.

Results

The results for Example 2 are shown in FIGS. 2 and 3. $IC_{50}$ values obtained from 5-LOX inhibition assay:

| Sample | Replication | $IC_{50}$ (µg/ml) | 95% confidence (µg/ml) |
|---|---|---|---|
| ViP_Matr'07_78 | 1 | 0.30 | 0.06 to 2.84 |
| ViP_Nig'07_8 | 1 | 3.00 | 1.33 to 10.76 |
| ViP_Matr'07_78 | 2 | 0.38 | 0.21 to 0.68 |
| ViP_Nig'07_8 | 2 | 3.02 | 1.57 to 5.82 |
| Mixture 1:1 | 1 | 0.53 | 0.23 to 1.24 |
| Reference | | $IC_{50}$ (nM) | 95% confidence (nM) |
| Dexamethasone | | 0.28 | 0.21 to 0.39 |

Example 3

Influence of NICHA 001 on the Proliferation of Human Cancer Cell Lines

The proliferative response of glioblastoma cells and prostate cancer cells under different concentrations of NICHA was investigated. Each experiment was done with *Nigella* oil, with chamomile oil and with a combination of both oils.

Samples

| Test samples | Description | Provider | Art. No | Batch No. | ViP Number |
|---|---|---|---|---|---|
| *Nigella* oil | Nigellae oleum | Hänseler AG | 26-4150-1 | 2006.08.0537 | ViP_Nig'07_8 |
| *Matricaria* essential oil | Matricariae Aetheroleum PhEur | Hänseler AG | 1-4925-2 | 2006.09.0181 | ViP_Matr'07_78 |

Assays

| Assays | Cell lines | Samples | Test concentrations |
|---|---|---|---|
| DNA synthesis | Prostate cancer cells | ViP_Nig'07_8 | 0.3/3/30 µg/ml |
| | DU145 | ViP_Matr'07_78 | 0.3/3/30/60 µg/ml |
| | Glioblastoma cells U-87 MG | ViP_Nig'07_8 | 0.3/3/30 µg/ml |
| | | ViP_Matr'07_78 Mixture | |

DNA Synthesis $^3$H-Thymidine incorporation: DU145 and U-87MG cells were harvested by trypsinisation and seeded at 10,000 cells/well in a 96 well plate. The cells were incubated with the samples at the required concentrations for 24 hrs and/or 48 hrs at 37° C. and 5% $CO_2$. The cells were pulsed with $^3$H-Thymidine (1 µCi/ml) (Perkin Elmer) for 24 hours. After which, they were washed with PBS and fixed twice with methanol for 5 min. The protein was precipitated by 0.3N TCA. After a washing step 150 µl 0.3N NaOH was added for 15 min to lyse the cells. Back ground controls were measured with the samples without cells.

To detect the incorporated $^3$H-Thymidine for the DNA synthesis the samples were transferred in scintillation tubes with scintillation cocktail. The quantification was performed in a Tri-Carb 1900 TR liquid scintillation counter (Packard, USA).

The effect of several concentrations of samples was measured by determining amount of radiolabel (dpm) under the assay conditions. Dose related values were expressed as a percentage of the positive control values. Sample points were measured as quadruplicates, errors are expressed as standard deviations.

Results Obtained for Prostate Cancer Cells DU145

The results of the effect of NICHA on DNA synthesis in prostate cancer cells (DU145) are shown in FIG. 4A-4D.

$IC_{50}$ values of the reference compounds on DNA synthesis are as follows:

| | 24 h incubation | | 48 h incubation | |
|---|---|---|---|---|
| Reference | $IC_{50}$ (nM) | 95% confidence (nM) | $IC_{50}$ (nM) | 95% confidence (nM) |
| Camptothecin | 152 | 115.9 to 199.4 | 7.5 | 5.1 to 11.0 |

Results Obtained for Glioblastoma Cells U87MG

Figure 5A:
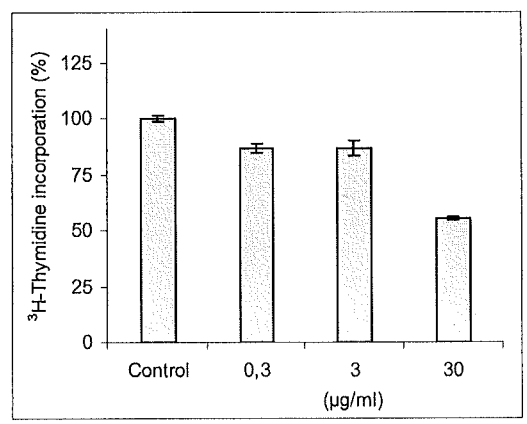
FIG. 5A: ViP_Matr'07_78 (Chamomile oil)
FIG. 5B: ViP_Nig'07_8 (*Nigella sativa* oil)
FIG. 5C: Mixture 1:1 (VIP_Matr'07_78: ViP_E_Nig'07_8)
Figure 5B:
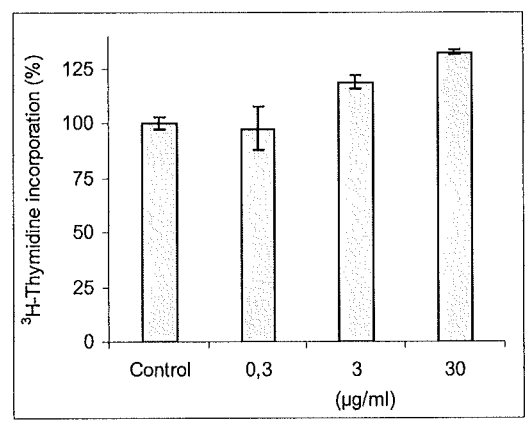
Figure 5C:
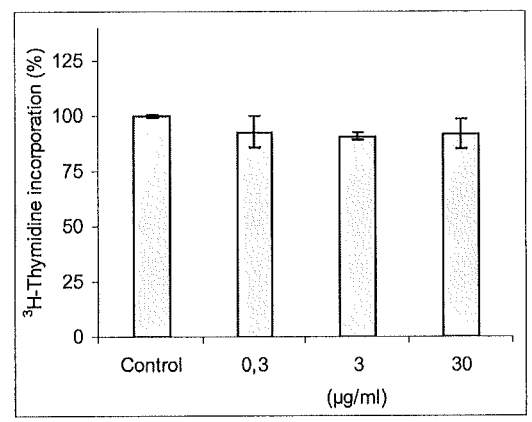

The results of the effect of NICHA on DNA synthesis in U-87MG cells (48 hours incubation) are shown in FIG. 5A-5C.

$IC_{50}$ values of the reference compounds on DNA synthesis with U-87MG cells are as follows:

| | 48 h incubation | |
|---|---|---|
| Reference | $IC_{50}$ (nM) | 95% confidence (nM) |
| Camptothecin | 3.32 | 2.5 to 4.4 |

Conclusions from the Results of the Examples

The essential oil of Chamomile (*Matricaria recutita*: VIP_Matr07_78) and the seed oil of Black Cumin (*Nigella sativa*: VIP_Nig07_8) were investigated regarding their potential to inhibit leucotriene synthesis in differentiated human granulocyte cell line HL 60 (human acute myeloid leukemia). *Nigella sativa* seed oil showed an impressive inhibition of 5-Lox activity with an IC 50 value of 3.02 ug/ml (Example 2, FIG. 2d). Surprisingly, a mixture of the two compounds inhibited the synthesis of leucotrienes in HL60 granulocyte cell line more than additive. Instead of the expected IC 50 of 0.76 ug/ml, an IC50 of 0.53 ug/ml resulted (Example 2, FIG. 2e). It may be concluded that a combination of the two compounds potentiates the activity of the single components.

VIP_Matr07_78 showed an even much higher inhibitory activity with respect to the inhibition of the leucotriene synthesis and revealed an IC 50 value of 0.38 ug/ml (Example 2, FIG. 2c). *Matricaria* essential oil seems therefore to be an extremely potent 5-LOX Inhibitor.

Figure 3A:
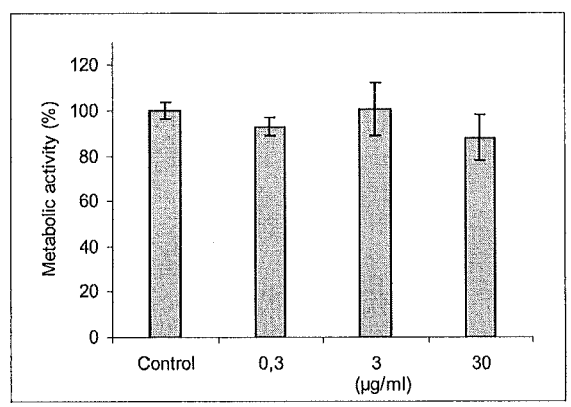
FIG. 3A: ViP_Matr'07_78 (Chamomile oil)
FIG. 3B: ViP_Nig'07_8 (*Nigella sativa* oil)
FIG. 4 shows the results obtained for the effect of NICHA on DNA synthesis in prostate cancer cells DU145 in Example 3.
Figure 3B:
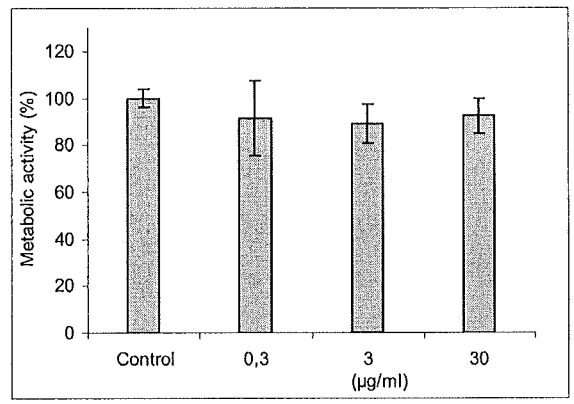
Figure 4A:
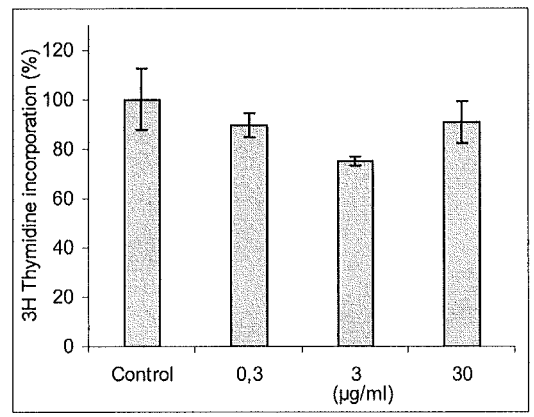
FIG. 4A: 24 hours incubation, ViP_Matr'07_78 (Chamomile oil)
FIG. 4B: 24 hours incubation, ViP_Nig'07_8 (*Nigella sativa* oil)
FIG. 4C: 48 hours incubation, ViP_Matr'07_78 (Chamomile oil)
FIG. 4D: 48 hours incubation, ViP_Nig'07_8 (*Nigella sativa* oil)
FIG. 5 shows the results obtained for the effect of NICHA on DNA synthesis in U-87MG cells at 48 hours incubation in Example 3.
Figure 4B:
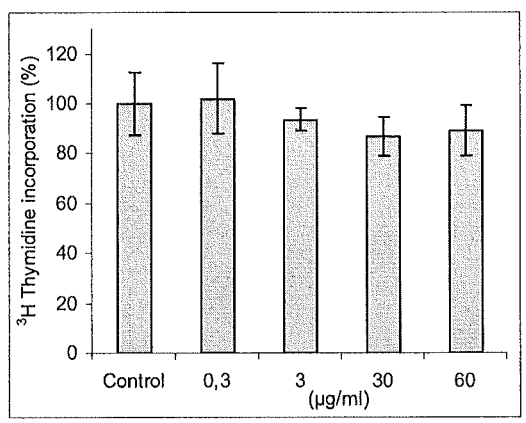
Figure 4C:
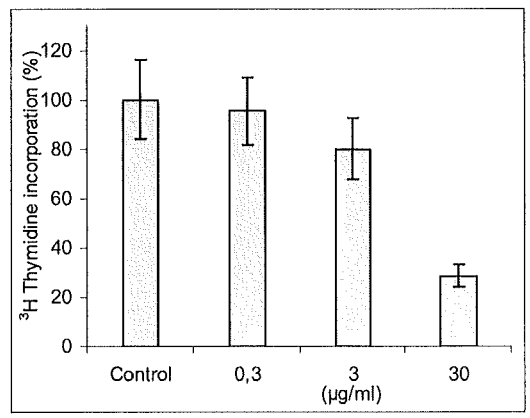
Figure 4D:
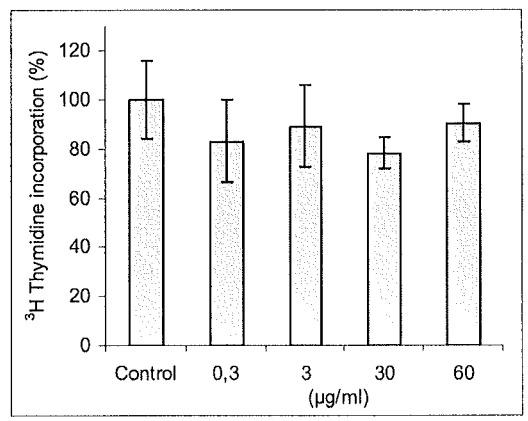

To evaluate whether the observed inhibitory activity is only a result of cytotoxic effects, the cells were incubated with the chosen concentrations for the 5-LOX experiments and the mitochondrial activity (WST) was measured. As shown in FIGS. 3a and 3b, no cytotoxicity occurred with VIP_Nig07_8 or with VIP_Matr07_78 at the chosen concentrations (Example 2, FIGS. 3a and 3b). It may be concluded that the observed activity to inhibit leucotriene synthesis is a result of a specific interaction with the 5-Lipoxygenase.

Further results were also obtained regarding interleukin 6 release by human macrophage cell line THP1. While *Nigella sativa* showed no activity (Example 1FIGS. 1c and 1d), *Matricaria recutita* inhibited interleukin 6 release from THP1 cells in a dose-dependent manner and an IC 50 value of 5 ug/ml (Example 1, FIGS. 1a and 1b)). Repetition experiments (Replication 2) showed the reproducibility of the results of Replication 1 (Example 1).

Figure 2A:
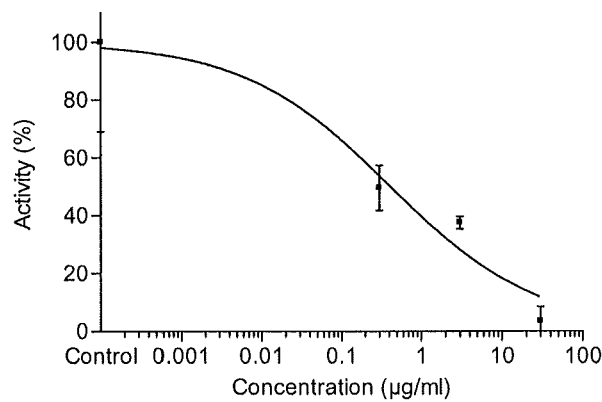
FIG. 2A: ViP_Matr'07_78 (Chamomile oil), Replication 1
FIG. 2B: ViP_Nig'07_8 (*Nigella sativa* oil), Replication 1
FIG. 2C: ViP_Matr'07_78 (Chamomile oil), Replication 2
FIG. 2D: ViP_Nig'07_8 (*Nigella sativa* oil), Replication 2
FIG. 2E: Mixture 1:1 (VIP_Matr'07_78: ViP_E_Nig'07_8)
FIG. 3 shows the results obtained from the viability assay on HL-60 cells with WST-1 under the influence NICHA in Example 2.
Figure 2B:
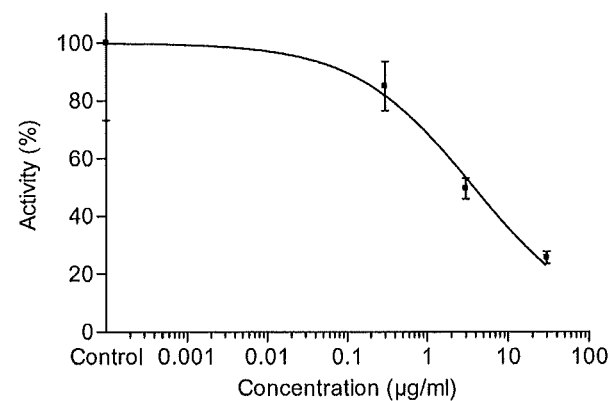
FIG. 2 shows the results obtained from the 5-LOX inhibition assay in Example 2 testing the inhibition of 5-LOX activity by NICHA (average of 2 to 4 independent assays (results from 3 independent 5-lox assays for ViP_E_Nig'07_8, 4 independent 5-lox assays for VIP_Matr'07_78 and 2 independent 5-lox assays for the Mixture 1:1).
Figure 2C:
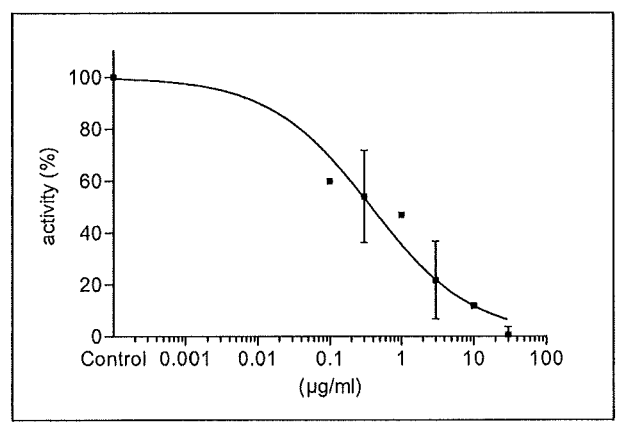
Figure 2D:
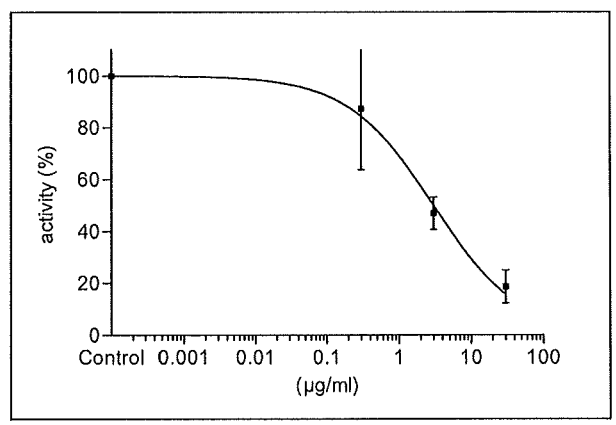
Figure 2E:
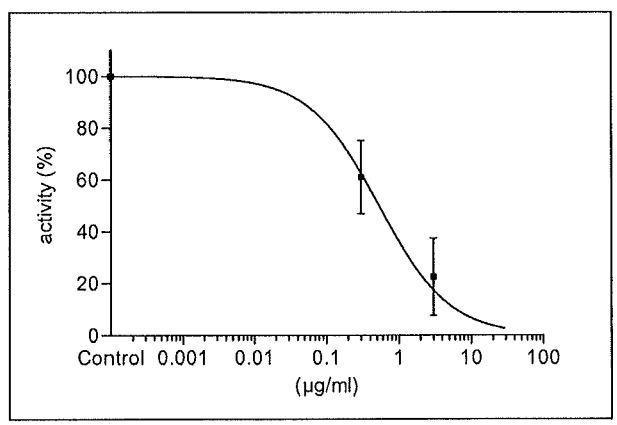

The results indicate that the essential oil of *Matricaria recutita* reveals strong inhibitory activity in respect of leucotriene synthesis in human acute myeloid leukemia cells HL60 (Example 2, FIG. 2c). Further, the results indicate that the release of interleukin 6 could be suppressed in human macrophage cell line THP1 (Example, FIGS. 1a and 1b).

As the concentrations necessary to obtain the inhibition effect are considerably low, it is speculated that therapeutically effective doses will be reached in men without difficulty, especially as essential oils are highly lipophilic and should be absorbed easily.

Taken together with the characteristic of the essential oil to effectively inhibit formation of eicosanoids (leucotrienes) with concentrations in the nanomolar range in human granulocyte cell line HL60, the essential oil of *Matricaria recutita* seems to be a very valuable candidate for the development of drugs for the treatment of inflammatory/autoimmune diseases and certain types of cancer.

A third set of experiments (Example 4) investigated whether the seed oil of *Nigella sativa* or the volatile oil of *Matricaria recutita* inhibits the DNA synthesis in the prostate cancer cell line DU 145 and the glioblastoma cell line U87MG in vitro. Whereas *Matricaria recutita* (VIP_Matr07_78) inhibited both cell lines after 48 hours with respect to DNA synthesis in a dose dependent manner (Example 4, FIG. 4c), *Nigella sativa* (VIP_Nig07_8) failed to show an inhibitory effect on both cancer cell lines (Example 4, FIG. 4d). As DU145 is known to produce interleukin 6 as a growth factor, it seems likely that suppression of the DNA synthesis is (at least partially) caused by the inhibitory activity on interleukin 6 release of the volatile oil of *Matricaria recutita*. The inhibition of the DNA synthesis of the glioblastoma cell line U87MG is apparently an effect of the strong suppression of leucotriene synthesis by the volatile oil of *Matricaria recutita*.

The invention claimed is:

1. A composition comprising:
   volatile oil of camomile flowers, and
   black cumin oil,
   wherein the volatile oil of chamomile flowers is obtained by water steam distillation that is carried out under reduced pressure and under a nitrogen atmosphere, and wherein the process further comprises the steps of:
   (i) contacting the water steam distillation composition with a cross-linked povidone to form a coumarin/povidone complex;
   (ii) removing the coumarin/povidone complex from the water steam distillation composition;
   (iii) removing water by contacting the remaining water steam distillation composition in step (ii) with anhydrous sodium sulphate; and
   (iv) separating the sodium sulfate from the composition obtained in step (iii).

2. The composition according to claim 1, containing less than 0.1% w/w water.

3. The composition according to claim 2, containing less than 0.01% w/w of coumarins, measured as 7-hydroxycoumarin.

4. The composition according to claim 2, which contains chamazulene in an amount of 5-15% w/w.

5. A pharmaceutical composition comprising the composition of claim 1 in a form suitable for oral, rectal, injectable or topical use.

6. The pharmaceutical composition of claim 5 for oral administration, in the form of tablets, trouches, lozenges, aqueous suspensions, oily suspensions, dispersible powders, dispersible granules, emulsions, hard capsules, soft capsules, syrups or elixers.

7. The pharmaceutical composition of claim 6 further comprising an agent selected from the group consisting of: excipients, sweetening agents, flavoring agents, coloring agents and preserving agents.

8. The pharmaceutical composition of claim 5 in the form of a suppository for rectal administration.

9. The pharmaceutical composition of claim 8, wherein said composition contains cocoa butter or polyethylene glycol.

10. The pharmaceutical composition of claim 5 in a form for topical administration, wherein said form is selected from the group consisting of creams, ointments, jellies, solutions or suspensions.

11. The pharmaceutical composition of claim 5 in the form of an oil-in-water emulsion, wherein the pharmaceutical composition further comprises:
   a) an oily phase comprising a vegetable oil, mineral oil or mixtures thereof,
   b) an emulsifying agent.

12. A composition comprising:
   the volatile oil of camomile flowers, and
   purified black cumin oil,
   wherein the black cumin oil is obtained by a process comprising the steps of:
   (i) contacting black cumin oil with a cross-linked povidone to form a phenolic/povidone complex;
   (ii) removing the phenolic/povidone complex from the water steam distillation composition;
   (iii) removing water by contacting the remaining water steam distillation composition in step (ii) with anhydrous sodium sulphate; and
   (iv) separating the sodium sulfate from the composition obtained in step (iii).

13. The composition according to claim 12, wherein the volatile oil of camomile flowers is obtained by filtration using a filter having a pore size of from 0.001 to 0.02 µm.

14. A pharmaceutical composition comprising the composition of claim 12 in a form suitable for oral, rectal, injectable or topical use.

15. The pharmaceutical composition of claim 14 for oral administration, in the form of tablets, trouches, lozenges, aqueous suspensions, oily suspensions, dispersible powders, dispersible granules, emulsions, hard capsules, soft capsules, syrups or elixirs.

16. The pharmaceutical composition of claim 15 further comprising an agent selected from the group consisting of: excipients, sweetening agents, flavoring agents, coloring agents and preserving agents.

17. The pharmaceutical composition of claim 14 in the form of a suppository for rectal administration.

18. The pharmaceutical composition of claim 17, wherein said composition contains cocoa butter or polyethylene glycol.

19. The pharmaceutical composition of claim 14 in a form for topical administration, wherein said form is selected from the group consisting of creams, ointments, jellies, solutions or suspensions.

20. The pharmaceutical composition of claim 14 in the form of an oil-in-water emulsion, wherein the pharmaceutical composition further comprises:
   a) an oily phase comprising a vegetable oil, mineral oil or mixtures thereof,
   b) an emulsifying agent.

\* \* \* \* \*